United States Patent [19]

Muller et al.

[11] Patent Number: 4,900,740

[45] Date of Patent: Feb. 13, 1990

[54] N,N'-DISUBSTITUTED GUANIDINES CONTAINING A CARBOXYL OR A TETRAZOLYL MOIETY

[75] Inventors: George W. Muller, Northbrook; Eric Walters, Mundelein; Grant DuBois, Lake Forest, all of Ill.

[73] Assignee: The NutraSweet Company, Deerfield, Ill.

[21] Appl. No.: 104,601

[22] Filed: Oct. 2, 1987

[51] Int. Cl.$^4$ .................... A61K 31/41; C07D 257/04
[52] U.S. Cl. ..................................... 514/381; 548/252; 548/254; 564/161; 564/163; 426/534; 426/535; 426/536; 426/537; 514/312
[58] Field of Search ............... 548/252, 254; 564/161, 564/163; 426/534, 535, 536, 537; 514/381, 312

[56] References Cited

U.S. PATENT DOCUMENTS

| | | | |
|---|---|---|---|
| 3,492,131 | 1/1970 | Schlatter | 426/548 |
| 3,535,336 | 10/1970 | Kornfeld | 548/496 |
| 3,615,700 | 10/1971 | Kornfeld | 424/49 |
| 3,899,592 | 8/1975 | Suarez et al. | 426/2 |
| 4,426,521 | 1/1984 | Tanaka et al. | 544/146 |
| 4,645,678 | 2/1987 | Nofre et al. | 426/548 |
| 4,673,582 | 6/1987 | Nofre et al. | 426/548 |
| 4,680,300 | 7/1987 | Nelson et al. | 514/312 |

FOREIGN PATENT DOCUMENTS

| | | |
|---|---|---|
| 1027113 | 2/1978 | Canada . |
| 0048051 | 3/1982 | European Pat. Off. . |
| 0195730 | 9/1986 | European Pat. Off. . |
| 0195731 | 9/1986 | European Pat. Off. . |
| 0241395 | 10/1987 | European Pat. Off. . |
| 8605320 | 4/1986 | France . |
| 8614607 | 10/1986 | France . |
| 8615788 | 11/1986 | France . |
| 8618233 | 12/1986 | France . |
| 8700539 | 1/1987 | France . |

OTHER PUBLICATIONS

Yuki and Inoue, The Reaction of Urea, Thiourea and S-Ethylisothiourea with Methyl Acrylate, Nippon Kagaku Kaishi, 1974, (11), 2140–43, (Translation), (Chemical Abstracts, 140061p, vol. 82, (1975)).

Lipinski, Bioisosterism in Drug Design, Annual Reports in Medicinal Chemistry, 21, 283–291, (1986).

Burger, A Guide to the Chemical Basis of Drug Design, History of Medicinal Chemistry, 28–30, 46, 84–87, (1983).

Thornber, Isosterism and Molecular Modification in Drug Design, 563–580, (1979).

Chemische Berichter, vol. 94, No. 7, 1961, pp. 1814–1824, Weinheim, D. E.; F. Micheel et al., (with translation).

Tsang et al., Peptide Sweeteners, 6, Structural Studies on the C-Terminal Amino Acid of L-Aspartyl Dipeptide Sweeteners, American Chemical Society, Jan. 3, 1984, 6 pages.

Ariyoshi et al., The Structure–Taste Relationships of the Dipeptide Esters Composed of L-Aspartic Acid and B-Hydroxy Amino Acids, Bulletin of the Chemical Society of Japan, 02/1974, pp. 326–330.

Tinti et al., Sweet Taste Receptor, Naturwissenschaften, 67, Jan. 2, 1980, pp. 193–194.

Tinti et al., Studies on Sweeteners Requiring the Simultaneous Presence of Both the $NO_2/CN$ and $COO^-$ Groups, Naturwissenschaften, 68, Dec., 1981, p. 143.

Miller et al., A Facile Conversion of Amino Acids to Guanidino Acids, Communications, Sep. 1986, 777–779.

Kawashima, J. Agricultural and Food Chem., vol. 28, No. 6, pp. 1338–1340, (1980).

*Primary Examiner*—Ronald W. Griffin
*Attorney, Agent, or Firm*—John M. Sanders

[57] ABSTRACT

N,N'-disubstituted guanidines containing a tetrazolyl or glycine moiety are provided as high potency sweetening agents.

43 Claims, No Drawings

N,N'-DISUBSTITUTED GUANIDINES CONTAINING A CARBOXYL OR A TETRAZOLYL MOIETY

BACKGROUND

The present invention relates to novel N,N'-disubstituted guanidine compounds useful as sweetening agents. Additionally, the present invention relates to sweetening compositions, food products containing the present N,N'-disubstituted guanidines, methods of sweetening foods, novel intermediates and methods of preparing the novel guanidines.

Certain guanidine derivatives are known in the art as sweeteners. See, for example, Yuki and Inoue (Nippon Kagaku Kaishi, no. 11, 2140–43 (1974)), Chemical Abstracts, Vol. 82, no. 140061p (1975) which describes N-((4-chlorophenylamino)iminomethyl)-β-alanine (Chemical Substance Index, vol. 76–85, 1972–1976, p. 1067cs); European patent application Ser. No. 0,107,597 published May 2, 1984 (U.S. Pat. No. 4,645,678); U.S. Pat. No. 4,673,582 and European patent application Ser. No. 0,195,730 published Sept. 24, 1986.

SUMMARY OF THE INVENTION

Briefly, in accordance with the present invention, N,N'-disubstituted guanidines, containing a carboxyl or a tetrazolyl moiety, are useful as sweetening agents. The present N,N'-disubstituted guanidines are added to food products in amounts sufficient to sweeten the food to a desired level. Typical food products include soft drinks, juices, condiments, candies, baked goods, chewing gum and pharmaceuticals.

The present N,N'-disubstituted guanidines are prepared by reacting a 5-aminoalkyl-substituted tetrazolyl or aminoalkylcarboxylic acids (glycine) with derivatives of thioureas. The resulting product is recovered and used in food applications to replace sucrose. The present N,N'-disubstituted guanidines can be combined with other sweeteners and bulking agents.

Of particular interest in the practice of the present invention, (1) N-cyclooctyl-N'-carboxymethyl-guanidine, (2) N-cyclohexyl-N'-tetrazol-5-yl-methyl-guanidine, (3) N-cyclooctyl-N'-tetrazol-5-yl-methyl-guanidine or mixtures of these three compounds are employed as a sweetening agent in foods especially in carbonated soft drinks.

DETAILED DESCRIPTION OF THE INVENTION

The present substituted guanidines are represented by the following formula:

$$\begin{array}{c} R_1 \diagdown \quad \diagup R_2 \\ N \quad\quad R_4 \\ | \quad\quad\quad | \\ HN=C-N-(CH)_nR_3 \\ | \\ H \end{array} \quad (I)$$

wherein $R_1$ is hydrogen, a $C_1$ to $C_4$ saturated, unsaturated, acyclic, cyclic or mixed hydrocarbyl or modified hydrocarbyl group and wherein, in the modified hydrocarbyl group,
1 to 2 atoms of carbon may be replaced by 1 to 2 of the same or different heteroatoms selected from the group consisting of N, O, S, Cl, Br and I,
and 1 to 3 atoms of hydrogen may be replaced by 1 to 3 atoms of fluorine;
wherein $R_2$ is a $C_1$ to $C_{13}$ saturated, unsaturated, acyclic, cyclic or mixed hydrocarbyl or modified hydrocarbyl group and wherein, in the modified hydrocarbyl group,
1 to 4 atoms of carbon may be replaced by 1 to 4 of the same or different heteroatoms selected from the group consisting of N, O, S, Cl, Br and I,
and 1 to 5 atoms of hydrogen may be replaced by 1 to 5 atoms of fluorine;
wherein $R_1$ and $R_2$ can be fused;
n is 0, 1, 2 or 3;
$R_3$ is —COOH or 5-substituted tetrazolyl

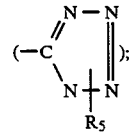

$R_4$ is H or $C_1$–$C_6$ alkyl with proviso that $R_4$ can only be alkyl on a single carbon atom when n=2 or 3; and
$R_5$ is H or $C_1$–$C_6$ alkyl wherein $R_5$ can be in the 1 or 2 position. When $R_5$ is in the 1 position, then the double bonds are as shown in Formula (I) and when $R_5$ is in the 2 position, then the double bonds are in the 3-4 and 1-5 positions.

The present N,N'-disubstituted guanidines include tautomeric forms and physiologically acceptable salts of the compounds of Formula I, above. Preferred compounds include those wherein $R_4$ and $R_5$ are hydrogen, n equals 1, and $R_3$ is 5-tetrazolyl.

It should be considered that by the term "modified hydrocarbyl" it is contemplated, as one example, that where $R_2$ is a $C_2$ modified hydrocarbyl group that one atom of carbon may be replaced by an atom of nitrogen so that the $C_2$ hydrocarbyl moiety may be replaced by the —CN cyano moiety. As a further example, it is contemplated that where $R_2$ is a $C_3$ modified hydrocarbyl group that one atom of carbon may be replaced by a nitrogen atom and two atoms of carbon may be replaced by two atoms of oxygen so that a $C_3$ hydrocarbyl moiety may be replaced by the —NO$_2$ (nitro) moiety. Other replacements of hydrocarbyl carbons by the same or different heteroatoms selected from the group consisting of N, O, S, Cl, Br, and I are similarly contemplated by the invention.

It should also be considered that the limitation that $R_2$ is a $C_1$ to $C_{13}$ group is established as a consequence of solubility limitations. It is contemplated that $R_2$ may be longer than the 13 carbon limitation stated above where other portions of the sweetening agent molecule or of the $R_2$ chain itself may be modified so as to provide for greater solubility.

Preferably, the present guanidine is one wherein $R_3$ is 5-tetrazolyl and $R_1$ is H or $CH_3$. Preferred guanidines also include those wherein $R_1$ is H and $R_2$ is cycoalkyl having 6 or more carbon atoms.

Preferred $R_2$ substituents include
normal alk(en)(yn)yl $C_2$–$C_{13}$,
branched alk(en)(yn)yl $C_3$–$C_{13}$,
cycloalk(en)yl $C_3$–$C_{13}$,
alk(en)yl cycloalk(en)yl $C_4$–$C_{13}$,
cycloalk(en)yl alk(en)yl $C_4$–$C_{13}$,
alk(en)yl cycloalk(en)yl alk(en)yl $C_5$–$C_{13}$,
alk(en)yl bicycloalk(en)yl $C_7$–$C_{13}$,
fused bicycloalk(en)yl $C_7$–$C_{13}$, alk(en)yl fused bicycloalk(en)yl $C_8$–$C_{13}$,
fused bicycloalk(en)yl alk(en)yl $C_8$–$C_{13}$,
alkenyl fused bicycloalk(en)yl alk(en)yl $C_9$–$C_{13}$,
fused tricycloalk(en)yl $C_{10}$–$C_{13}$,
alk(en)yl fused tricycloalk(en)yl $C_{11}$–$C_{13}$,
fused tricycloalk(en)yl alk(en)yl $C_{11}$–$C_{13}$ or
alk(en)yl fused tricycloalk(en)yl alk(en)yl $C_{11}$–$C_{13}$.

Particularly preferred are those guanidines wherein $R_2$ is selected from the group consisting of cyclooctyl, benzyl, cyclononyl, phenyl, alpha-phenethyl, cycloheptyl and cyclohexyl.

Preferred guanidines also include those listed above wherein $R_2$ is a modified hydrocarbyl group wherein up to four carbon atoms may be replaced by the same or different heteroatoms selected from a group consisting of S to replace C or $CH_2$, N to replace CH, NH and O to replace $CH_2$ and Cl, Br and I to replace $CH_3$ and wherein up to 5 atoms of hydrogen may be substituted by fluorine atoms. Also preferred are those sweetening agents wherein $R_2$ is selected from the group consisting of $CH(CH_3)C_6H_5$, pyridinyl, piperidyl, homopiperidyl, indolyl, indolinyl, isoindolinyl, quinolyl, isoquinolyl, pyrazinyl, pyrimidyl, indazolyl, quinoxalinyl, quinazolinyl, purinyl, $CH_2C_6H_5$, pyranyl, benzofuranyl, methoxyphenyl, methyloxycarbonylphenyl, 3-methylphenyl, 3-cyanophenyl, 3-chlorophenyl, 3,5-dimethylphenyl, 3,5-dichlorophenyl, 3,4,5-trichlorophenyl, 3-bromophenyl, 3,4-methylenedioxyphenyl, morpholinyl, benzoxazolyl, acetamidophenyl, thiophenyl, benzothiophenyl, 2,2,4,4-tetramethylthiacyclobut-3-yl, thiazolyl, isothiazolyl, $SO_2C_6H_5$, alkyl substituted $—SO_2C_6H_5$ (2,4,6-trimethylbenzenesulfonyl and 2,4,6-triisopropylbenzenesulfonyl), $SO_2$c-$C_6H_{11}$ and $SO_2$c-$C_7H_{13}$.

Other preferred compounds include those having the formula

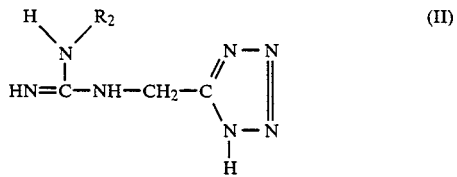

(II)

wherein $R_2$ is as described above. Particularly preferred compounds are those of Formula II wherein $R_2$ represents $C_8$–$C_{10}$ cycloalkyl.

Most preferred are such compounds of Formula I wherein $R_1$ and $R_4$ are H; $R_3$ is 5-tetrazolyl; and wehrein $R_2$ is selected from the group consisting of $CH(CH_3)C_6H_5$, $CH_2C_6H_5$, $CH(CH_3)$-c-$C_6H_{11}$, c-$C_6H_{11}$, c-$C_7H_{13}$, c-$C_8H_{15}$, c-$C_9H_{17}$, c-$C_{10}H_{19}$, $SO_2C_6H_5$, alkyl substituted $SO_2C_6H_5$ and $SO_2C_7H_{13}$.

The present invention also includes physiologically acceptable salts of the present guanidines including sulfate, phosphate, citrate, hydrochloride, sodium, potassium, ammonium, calcium and magnesium salts.

Additionally, the present invention relates to edible products containing the present guanidine compounds as sweetening agents either alone or in combination with other sweeteners such as carbohydrate sweeteners or high potency sweeteners. In combinations with other sweeteners, the present N,N'-disubstituted guanidines may provide from about 10 to about 90 percent of the sweetness, advantageously from 25–75 percent of the sweetness and preferably 40–60 percent of the sweetness. Also provided by the present invention is a process for sweetening edible products such as foods, beverages, candies, chewing gums, sweets, pharmaceuticals, veterinary preparations and the like.

The present invention further contemplates the present N,N'-disubstituted guanidines in combination with other sweetening agents and/or physiologically acceptable carriers which may be a bulking agent. Suitable carriers include polydextrose, starch, maltodextrins, cellulose, methylcellulose, maltitol, carboxymethylcellulose, hydroxymethylcellulose, microcrystalline cellulose, sodium alginate, pectins, gums, lactose, maltose, glucose, leucine, glycerol, mannitol, sorbitol, sodium bicarbonate and phosphoric, citric, tartaric, fumaric, benzoic, sorbic, propionic acids and their sodium, potassium and calcium salts and mixtures of all of the above.

Suitable sweetening agents which may be used in combination with the present N,N'-disubstituted guanidines can be sugar or high potency sweeteners such as, for example, sucrose, corn syrups, fructose, high fructose corn syrup, aspartame, alitame, neohesperidin dihydrochalcone, hydrogenated isomaltulose, stevioside, L-sugars, glycyrrhizin, xylitol, acesulfam-K, saccharin (sodium, potassium or calcium salt), cyclamic acid (sodium, potassium or calcium salt), trichlorogalactosucrose (TGS or sucralose), monellin and thaumatin and mixtures thereof.

The present invention also relates to a method of preparing the tetrazolyl and carboxyl containing guanidine compounds. The substituted guanidines of the present invention are prepared employing synthetic methods which are analogous to known methods disclosed in the literature. These known methods have been summarized in recent papers by Maryanoff (C. Maryanoff, R. C. Stanzione, J. N. Plampin, and J. E. Mills, J. Org. Chem. 1986, 51, 1882–1884) and A. E. Miller, J. J. Bischoff, Synthesis, 1986, 777–179. The techniques are further described in J. Med. Chem., 1978, no. 21, pp. 773–781; U.S. Pat. No. 4,673,582; Chem. Ber. 1966, 99, 1252-157; U.K. Pat. No. 1587 258; J. Org. Chem., 1970, 35, pp. 2067–2069; J. Org. Chem. 1986, no. 56, 1882–1884; Chem. Ber. 1967, 100, pp. 591–604; J. fur Prakt. Chem. 1977, 319, pp. 149–157; EPO patent application Ser. No. 0,195,730 published 24 September 1986; and The Chemistry of Amidines and Imidates, S. Patai, ed. Wiley-Interscience 1975, pp. 283–348, all of which are incorporated by reference. One general technique is particularly useful. It involves formation of a thiourea derivative, i.e., sulfonic acid derivatives of a thiourea. These intermediates are reacted with a 5-aminoalkyl-substituted tetrazolyl or an aminoalkylcarboxylic acid (glycine) resulting in formation of the present N,N'-disubstituted guanidines. The preparation of 5-substituted tetrazolyls is described by Grzonka and Liberek in Roczniki Chemii, Ann. Soc. Chim. Polonorum, 45, 967–986 (1971), which is incorporated herein by reference.

In general, a reactive intermediate, with an easily liberated activating moiety (leaving group), designated by the letter L in the following reactants, can be employed wherein the intermediate contains appropriately substituted amine groups corresponding to the substituents present in the guanidine nitrogens. The leaving groups are preferably selected from the group consisting of S-alkyl (isothiourea), O-alkyl (isourea), $OSO_2$-aryl, $SO_3H$ and halogen moieties. As a general principle, a reaction is brought about between the reactant intermediate and the appropriate complementary amine, that is to say, the following compounds are brought into contact with one another:

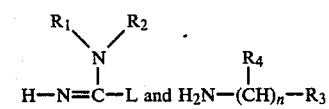     (1)

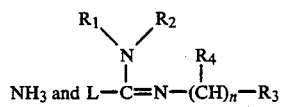     (2)

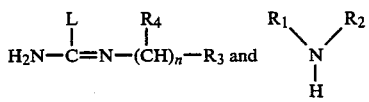     (3)

These reactions can be carried out in water or in organic solvents such as ethanol, methanol, acetone, chloroform, carbon tetrachloride or pyridine at a temperature which may vary from ambient temperature to boiling. The choice of the solvent and the temperature employed will depend on the L group and the reactivity of the amine employed and can be readily determined by one skilled in the art. The above reactions are employed to make both the carboxylic acid guanidines and the tetrazolyl guanidines of the present invention by employing starting materials wherein $R_3$ is 5-tetrazolyl or —COOH.

Additionally, the present invention encompasses novel intermediates used in preparing the present guanidine compounds as seen in the tetrazolyl and glycine containing reactants in (3) above.

Various methods may be employed to prepare the intermediaries but the corresponding thiourea derivative will generally have to be prepared as follows, for example:

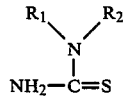

One of the preferred methods of synthesis employed to obtain these thiourea derivatives consists of allowing an alkyl or aryl isothiocyanate to react with $NH_3$ or $NH_4OH$. The reaction is conducted from ambient temperature to boiling, depending on the reciprocal reactivity of the two compounds and takes place in an organic solvent such as ethanol, ethyl acetate, acetonitrile, chloroform or acetone. These reactions can be characterized as follows:

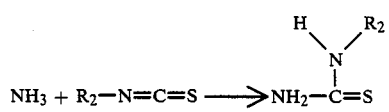

The preferred method consists of transforming thiourea derivatives obtained in this way into S-alkyl or sulfonic acid derivatives (L=$SO_3H$). Preferred L leaving groups include S—$CH_3$ and $SO_3H$, such as in the following compound, for example:

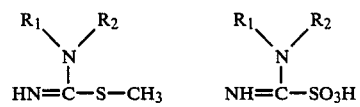

The S-alkyl intermediates are obtained by treating the corresponding thiourea derivative with an alkylating agent (such as methyl iodide or dimethyl sulfate) in solution in an organic solvent such as acetone or 2-butanone at a temperature ranging from ambient temperature to boiling depending upon reactivity of the materials. The S-methylisothiourea derivatives are thus obtained in the form of salts (iodide or sulfate). These salts are next treated in a solution of sodium hydroxide or potassium hydroxide in order to generate their free base form. They are next condensed with an aminomethyltetrazolyl, tetrazolyl or glycine in a suitable solvent, at a temperature ranging from ambient to boiling depending on reactivity of the materials.

Method 1: The Isothiourea Route:

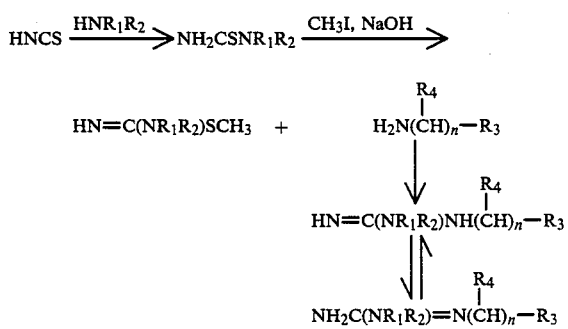

Method 2: Sulfonic Acid Route

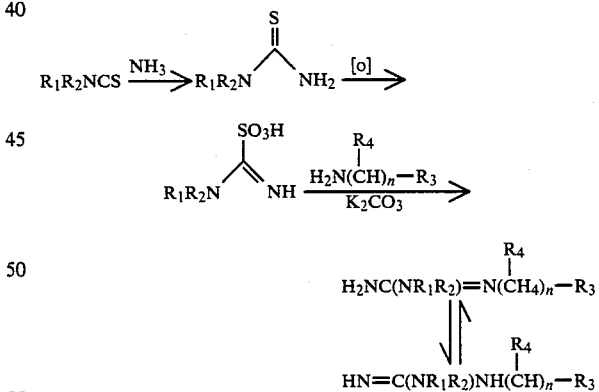

According to the sulfonic acid method, an alkylisothiocyanate is allowed to condense with $NH_3$ or $NH_4OH$ preferably at ambient temperature and in an organic solvent to yield a thiourea $NH_2CSNR_1R_2$. The thiourea is purified by recrystallization or other standard procedures and is then oxidized [o] with, for example, $H_2O_2$ or $H_2O_2/Na_2MoO_4$. This reaction is conducted in an organic solvent or $H_2O$ at temperatures varying from 0°–40° C. depending on thiourea reactivity. The isothiourea is then reacted with the aminoalkyltetrazolyl or aminoalkylcarboxylic acid (glycine) to give the guanidine

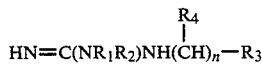

This reaction may be conducted in water or organic solvents and at temperatures varying from ambient to 100° C. The guanidine is then purified by recrystallization or other standard methods.

The present N,N-disubstitued guanidines may exist as an equilibrium mixture of tautomeric forms. All tautomers of the guanidines are contemplated by the present invention. The guanidines are shown in the general formula as the tautomer with

unsaturation; however, this tautomer is invariably in equilibrium with the other tautomers, i.e.,

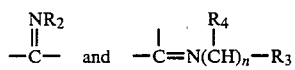

When $R_3$ is 5-tetrazolyl and $R_5$ is alkyl, the present N,N'-disubstituted guanidines are converted into salts by reacting them with physiologically acceptable acids such as HCl, sulfuric acid, phosphoric acid, citric acid and the like. When $R_5$ is hydrogen, the sweetening agents according to the present invention may exist in Zwitterion or in acid form. They can thus be converted into salts by acids or by physiologically acceptable organic or inorganic bases. A preferred method of preparing such salts consists of concentrating to dryness in vacuo a mixture of a compound according to the present invention in an aqueous solution with an equivalent amount of an acid or of an organic or inorganic base. The preferred salts according to the present invention are hydrochloride or sodium, potassium, ammonium, calcium, phosphate, citrate or magnesium salts.

The present sweetening agents may take the form of a balanced mixture of tautomeric forms. Thus, the following tautomeric forms may be obtained, when $R_1$ is H:

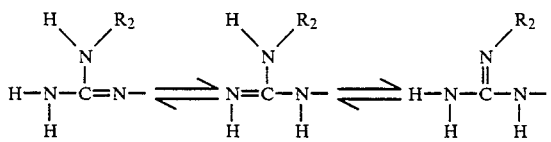

or when $R_1 = CH_3$:

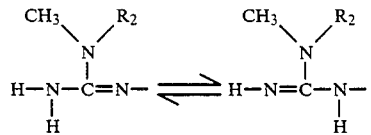

or when $R_5$ is H, then the following will apply:

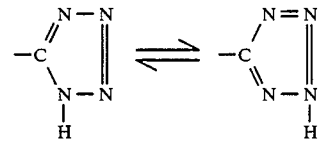

The present N,N'-disubstituted guanidines are represented in Formula (I) by a single tautomeric form with the full knowledge that the tautomeric form must necessarily be in balance with the other tautomeric forms, depending on the nature of the substituents $R_1$, $R_2$ and $R_5$ as well as on the pH.

The present N,N'-disubstituted guanidines may have an assymetrical carbon atom, i.e., optically active site. These compounds exist in (R) and (S) enantiomeric forms. Both the (R) and (S) enantiomers of the N,N'-disubstituted guanidines are contemplated by the present invention.

The present invention also relates to a method of sweetening foods or comestible products. In such uses, the present N,N'-disubstituted guanidines are added to any consumable product in which it is desired to have a sweet taste. The present sweetening agents are added to such products in amounts effective to impart the desired level of sweetness. The optimum amount of sweetening agent will vary depending on a variety of factors such as, for example, the sweetness potency of the particular sweetening agent, storage and use conditions of the product, the particular components of the products, the flavor profile of the comestible products and the level of sweetness desired. One skilled in the art can readily determine the optimum amount of sweetening agent to be employed in a particular formulation of a food product by conducting routine sweetness (sensory) experiments. Usually, the present sweetening agents are added to the comestible products in amounts of from about 0.001 to about 0.5 percent by weight of the comestible product, advantageously from about 0.005 to about 0.25 weight percent and preferably from about 0.01 to about 0.2 weight percent. Concentrates, of course, will contain higher percentages of sweetening agent(s), and are diluted for end use purposes.

Suitable products which are sweetened by the present sweetening agents include any products for which a sweet flavor component is desired such as food products (for human or animal consumption), beverages (alcoholic, soft drinks, juices, carbonated beverages), confectionary products (candies, chewing gum, baked goods, pastries, breads, etc.), hygiene products, cosmetics, pharmaceutical products and veterinary products. In sweetening chewing gum, the present N,N'-disubstituted guanidines can be added in amounts in excess of a sucrose equivalent normally found in chewing gum. This excess amount of guanidine sweetener provides a longer sweet taste and enhancement of flavor (flavor enhancer) as a result of having a slower dissolution rate and lower solubility when compared to sucrose.

The present N,N'-disubstituted guanidines can be added in pure form to foods to impart a sweet flavor. However, because of the high sweetness potency of the present sweetening agents, they are typically admixed with a carrier or bulking agent. Suitable carriers or bulking agents include polydextrose, starch, malto-dextrins, cellulose, methylcellulose, carboxymethylcellulose, hydroxymethylcellulose, microcrystalline cellulose, cellulose derivatives, sodium alginate, pectins, gums, lactose, maltose, maltitol, glucose, leucine, glycerol, mannitol, sorbitol, sodium bicarbonate and phosphoric, citric, tartaric, fumaric, benzoic, sorbic and propionic acids and their sodium, potassium and calcium salts and mixtures of all of the above.

The present N,N'-disubstituted guanidines can be employed alone as the sole sweetening agent in a comestible product. Mixtures of the present N,N'-disubstituted guanidines can also be employed. Additionally, the present N,N'-disubstituted guanidines can be used in combination with other sweetening agents such as sugars (such as sucrose and fructose), corn syrups, dipeptide sweeteners such as aspartame and alitame and other sweeteners such as glycyrrhizin, aminoacyl sugars, xylitol, sorbitol, mannitol, acesulfam K, thaumatin, monellin, cyclamates, saccharin, neohesperidin dihydrochalcone, hydrogenated isomaltulose, stevioside, L-sugars, trichlorogalactosucrose (TGS), and mixtures thereof.

The following example illustrates the practice of the present invention but should not be construed as limiting its scope.

EXAMPLE 1:

Synthesis of N-cyclooctyl-N'-carboxymethyl-guanidine:

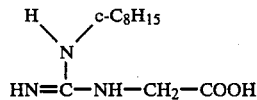

Step 1: N-Cyclooctylthiourea

To a stirred solution of cyclooctyl isothiocyanate (7.26 g, 42.9 mmol) in 70 ml of $CH_3CN$ was added 8.5 ml of 15N $NH_4OH$ (130 mmol). The reaction progress was monitored by thin layer chromatography (TLC); 1/1 EtOAc/hexane. After 3 days, the reaction solution was concentrated, dissolved in 50 ml of ethyl acetate and washed with water (25 ml) and brine (aqueous saturated NaCl) (3×25 ml ea.). The organic layer was dried ($Na_2SO_4$) and concentrated. The residue was purified by flash chromatography (silica gel, 3/7 EtOAc/hexane) to yield 6.25 g (78.2%) of the desired thiourea. PMR($CDCl_3$)ppm 6.5 (bs, 1H), 6.00 (s, 2H), 4.35 (bs, 1/2H), 3.45 (bs, 1/2H), 2.1–1.3 (m, 14H). The melting point (MP) was 93°–95° C.

Step 2: N-Cyclooctylaminoiminomethanesulfonic acid

To a stirred suspension of N-cyclooctylthiourea (2.42 g, 13.0 mmol) from Step 1, NaCl (0.29 g, 10 mmol) and $Na_2MoO_4\cdot 2H_2O$ (50 mg, 0.2 mmol) in 6 ml of water, cooled in an ice bath, was added 4.2 ml of 30% $H_2O_2$ (41 mmol) dropwise over 30 minutes. A thick slurry resulted which was diluted with an additional 6 ml of water and allowed to warm to room temperature (RT). The reaction mixture exothermed to 40° C. on warming. After the temperature began dropping, the reaction mixture was cooled to 10° C., and the resulting solid isolated by filtration. The white solid was washed with brine, water, and then air-dried to yield 2.73 g (89.5%) of the desired product. PMR(dmso-d6)ppm 9.41, 9.39 (2s, 1H), 9.13, 9.05 (2s, 2H), 3.67 (m, 1H), 1.9–1.1 (m, 14H). IR(KBr) cm-1 3410, 3280, 3160, 2920, 1700, 1620, 1360, 1160. MP: 141°–143° C. decomp. Anal. for $C_9H_{18}N_2O_3S\cdot 0.83\ H_2O$: C, 43.37; H, 7.95; N, 11.238. Found: C, 43.36; H, 8.02; N, 11.15.

Step 3: N-Cyclooctyl-N'-carboxymethyl-guanidine

To a stirred solution of glycine (0.321 g, 4.27 mmol) and $K_2CO_3$ (0.590, 4.27 mmol) in 4.5 ml of water was added N-cyclooctylaminoiminomethanesulfonic acid (1.00 g, 4.27 mmol) from Step 2 in small portions over 5 minutes, followed by 3.5 ml of water. After 22 hours, the reaction was refluxed for 2 hours. The reaction was allowed to cool to RT, and the resulting suspension was filtered. The white precipitate was washed with water and air-dried. The resulting white powder was sonicated in $CH_2Cl_2$, filtered and dried to yield 0.385 g (40.0%) of the desired guanidine. PMR ($CD_3CO_2D$)ppm 4.05 (s, 2H), 3.65 (tt, 1H), 2.0–1.2 (m, 14H). Calcd. Anal. for $C_{11}H_{21}N_3O_2$: c, 58.125; H, 9.312; N, 18.486. Found: C, 58.20; H, 9.42; N, 18.44. MP:>240° C. decomp. An aqueous solution of this disubstituted guanidine (0.01 wt. %) was sweet when tasted.

Table I below lists various compounds according to the present invention.

TABLE I $$\begin{array}{c} H \diagdown \quad \diagup R_2 \\ N \\ | \\ HN=C-NH-CH_2-R_3 \end{array}$$

| Cpd. | $R_3$ | $R_2$ |
|---|---|---|
| 1 | —COOH | c-$C_8H_{15}$ |
| 2 | —COOH | c-$C_6H_{11}$ |
| 3 | —COOH | (S)CH($CH_3$)$C_6H_5$ |
| 4 | —COOH | (S)CH($CH_3$)$C_6H_5$ |
| 5 | —COOH | (S)CH($CH_3$)$C_6H_5$ |
| 6 | —COOH | (S)CH($CH_3$)$C_6H_5$ |
| 7 | —COOH | (S)CH($CH_3$)$C_6H_5$ |
| 8 | —COOH | $CH_2C_6H_5$ |
| 9 | —COOH | 1-naphthyl |
| 10 | —COOH | $SO_2C_6H_5$ |
| 11 | —COOH | c-$C_6H_{11}$ |
| 12 | —COOH | c-$C_8H_{15}$ |
| 13 | —COOH | $CH_3$ |
| 14 | —COOH | $CH_2C_6H_5$ |
| 15 | —COOH | $SO_2C_6H_5$ |
| 16 | 5-tetrazolyl | c-$C_8H_{15}$ |
| 17 | 5-tetrazolyl | c-$C_6H_{11}$ |
| 18 | 5-tetrazolyl | (S)CH($CH_3$)$C_6H_5$ |
| 19 | 5-tetrazolyl | (S)CH($CH_3$)$C_6H_5$ |
| 20 | 5-tetrazolyl | (S)CH($CH_3$)$C_6H_5$ |
| 21 | 5-tetrazolyl | (S)CH($CH_3$)$C_6H_5$ |
| 22 | 5-tetrazolyl | (S)CH($CH_3$)$C_6H_5$ |
| 23 | 5-tetrazolyl | $CH_2C_6H_5$ |
| 24 | 5-tetrazolyl | 1-naphthyl |
| 25 | 5-tetrazolyl | $SO_2C_6H_5$ |
| 26 | 5-tetrazolyl | c-$C_6H_{11}$ |
| 27 | 5-tetrazolyl | c-$C_8H_{15}$ |
| 28 | 5-tetrazolyl | $CH_3$ |
| 29 | 5-tetrazolyl | $CH_2C_6H_5$ |
| 30 | 5-tetrazolyl | $SO_2C_6H_5$ |

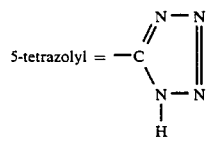

In similar operations, the various guanidine compounds described in formula I are prepared and are used to sweeten food products.

What is claimed is:

1. A compound corresponding to the formula,

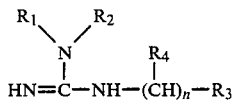

wherein $R_1$ is an atom of hydrogen or $R_1$ is a $C_1$ to $C_4$ saturated, unsaturated, acyclic, cyclic or mixed hydrocarbyl or modified hydrocarbyl group and wherein, in the modified hydrocarbyl group,
- 1 to 2 atoms of carbon may be replaced by 1 to 2 of the same or different heteroatoms selected from the group consisting of N, O, S, Cl, Br and I,
- and 1 to 3 atoms of hydrogen may be replaced by 1 to 3 atoms of fluorine;

wherein $R_2$ is a $C_1$ to $C_{13}$ saturated, unsaturated, acyclic, cyclic or mixed hydrocarbyl or modified hydrocarbyl group and wherein, in the modified hydrocarbyl group,
- 1 to 4 atoms of carbon may be replaced by 1 to 4 of the same or different heteroatoms selected from the group consisting of N, O, S, Cl, Br and I,
- and 1 to 5 atoms of hydrogen may be replaced by 1 to 5 atoms of fluorine;

n is 0, 1, 2, or 3;
wherein $R_1$ and $R_2$ can be fused;

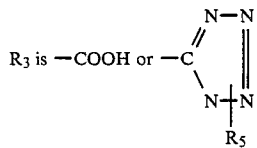

wherein $R_4$ is H or $C_1$–$C_6$ alkyl with the proviso that $R_4$ can only be alkyl on a single carbon atom when n=2 or 3;

$R_5$ is H or $C_1$–$C_6$ alkyl; and tautomers and physiologically acceptable salts thereof.

2. The compound of claim 1 wherein $R_1$ is H.

3. The compound of claim 1 wherein $R_3$ is -5-tetrazolyl and $R_1$ is H.

4. The compound of claim 3 wherein $R_4$ is H and n is 1.

5. The compound of claim 1 wherein $R_5$ is H.

6. The compound of claim 1, 2, 3, 4 or 5 wherein $R_2$ is a cycloalkyl having more than 6 carbon atoms.

7. The compound of claim 1, 2, 3, 4 or 5 wherein $R_2$ is cyclooctyl, alpha-phenethyl or $SO_2C_6H_5$.

8. The compound of claim 1, 2, 3, 4 or 5 wherein $R_2$ is selected from the group consisting of
- Normal alk(en)(yn)yl $C_2$–$C_{13}$,
- Branched alk(en)(yn)yl $C_3$–$C_{13}$,
- Cycloalk(en)yl $C_3$–$C_{13}$,
- Alk(en)yl cycloalk(en)yl $C_4$–$C_{13}$,
- Cycloalk(en)yl alk(en)yl $C_4$–$C_{13}$,
- Alk(en)yl cycloalk(en)yl alk(en)yl $C_5$–$C_{13}$,
- Alk(en)yl bicycloalk(en)yl $C_7$–$C_{13}$,
- Fused bicycloalk(en)yl $C_7$–$C_{13}$,
- Alk(en)yl fused bicycloalk(en)yl $C_8$–$C_{13}$,
- Fused bicycloalk(en)yl alk(en)yl $C_8$–$C_{13}$,
- Alkenyl fused bicycloalk(en)yl alk(en)yl $C_9$–$C_{13}$,
- Fused tricycloalk(en)yl $C_{10}$–$C_{13}$,
- Alk(en)yl fused tricycloalk(en)yl $C_{11}$–$C_{13}$,
- Fused tricycloalk(en)yl alk(en)yl $C_{11}$–$C_{13}$ and
- Alk(en)yl fused tricycloalk(en)yl alk(en)yl $C_{11}$–$C_{13}$.

9. The compound of claim 8 wherein $R_2$ is selected from the group consisting of n-$C_5H_{11}$, n-$C_6H_{13}$, n-$C_7H_{15}$, $CH(CH_3)(CH_2)_2CH_3$, $CH(CH_3)(CH_2)_3CH_3$, $(CH_2)_3CH(CH_3)_2$, $(CH_2)_4CH(CH_3)_2$, $(CH_2)_5CH(CH_3)_2$, $C_6H_5$, $C_6$–$C_{10}$ cycloalkyl, $CH_2C_6H_5$, $CH_2$-c-$C_6H_{11}$, $CH(CH_3)C_6H_5$, $CH(CH_3)$-c-$C_6H_{11}$, $(CH_2)_2C_6H_5$, $(CH_2)_2$-c-$C_6H_{11}$, $CH(CH_3)CH_2C_6H_5$, $CH(CH_3)CH_2$-c-$C_6H_{11}$, $C_6H_4(CH_3)$, $C_6$–$C_{10}$ cycloalkyl$(CH_3)$, $CH_2C_6H_4(CH_3)$, $CH_2$-c-$C_6H_{10}(CH_3)$, $CH(CH_3)C_6H_4(CH_3)$, $CH(CH_3)$-c-$C_6H_{10}(CH_3)$, $(CH_2)_2CH(c$-$C_3H_5)_2$, $(CH_2)_3CH(c$-$C_3H_5)_2$, $CH(CH_3)CH_2CH(c$-$C_3H_5)_2$, $CH(CH_3)(CH_2)_2CH(c$-$C_3H_5)_2$, naphthyl, 5,6,7,8-tetrahydronaphthyl, perhydronaphthyl, indenyl, indanyl, naphthyl$(CH_3)$, 5,6,7,8-tetrahydronaphthyl$(CH_3)$, perhydronaphthyl$(CH_3)$, indenyl$(CH_3)$, indanyl$(CH_3)$, fenchyl, $CH_2$-naphthyl, $CH_2$-5,6,7,8-tetrahydronaphthyl, $CH_2$-perhydronaphthyl, $CH_2$-indenyl, $CH_2$-indanyl, $CH_2$-naphthyl$(CH_3)$, $CH_2$-5,6,7,8-tetrahydronaphthyl$(CH_3)$, $CH_2$-perhydronaphthyl$(CH_3)$, $CH_2$-indenyl$(CH_3)$, $CH_2$-indanyl$(CH_3)$, adamantyl, $CH_2$-adamantyl, $CH(CH_3)$adamantyl, and $CH_2$-adamantyl$(CH_3)$.

10. The compound of claim 1, 2, 3, 4 or 5 wherein $R_2$ is a modified hydrocarbyl group wherein up to four carbon atoms may be replaced by the same or different heteroatoms selected from a group consisting of
- S to replace C or $CH_2$,
- N to replace CH or $CH_3$,
- NH and O to replace $CH_2$ and
- Cl, Br and I to replace $CH_3$, wherein up to 5 atoms of hydrogen may be substituted by fluorine atoms.

11. The compound of claim 10 wherein $R_2$ is selected from the group consisting of
- $N(CH_3)C_6H_5$, pyridinyl, piperidyl, homopiperidyl, indolyl, indolinyl, isoindolinyl, quinolyl, isoquinolyl, pyrazinyl, pyrimidyl, indazolyl, quinoxalinyl, quinazolinyl, purinyl,
- $CH_2C_6H_5$, pyranyl, benzofuranyl, methoxyphenyl, methyloxycarbonylphenyl, 3,4-methylenedioxyphenyl, morpholinyl, benzoxazolyl, acetamidophenyl, cyano, nitro,
- thiophenyl, benzothiophenyl, 2,2,4,4-tetramethylthiacyclobut-3-yl, thiazolyl, isothiazolyl, $SO_2C_6H_5$, alkyl substituted $SO_2C_6H_5$, $SO_2$c-$C_6H_{11}$ and $SO_2$c-$C_7H_{13}$.

12. The compound of claim 1 having the formula

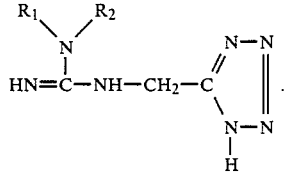

13. The compound of claim 12 wherein $R_1$ is H.

14. The compound of claim 12 wherein $R_1$ is $CH_3$.

15. The compound of claim 12 wherein $R_2$ is selected from the group consisting of $CH(CH_3)C_6H_5$, $CH_2C_6H_5$, $CH(CH_3)$-c-$C_6H_{11}$, c-$C_6H_{11}$, c-$C_7H_{13}$, c-$C_8H_{15}$, c-$C_9H_{17}$, c-$C_{10}H_{19}$, $SO_2C_6H_5$ and $SO_2$c-$C_7H_{13}$.

16. The compound of claim 12 wherein $R_1$ is selected from the group consisting of H and $CH_3$ and wherein $R_2$ is selected from the group consisting of $CH(CH_3)C_6H_5$, $CH_2C_6H_5$, $CH(CH_3)$-c-$C_6H_{11}$, c-$C_6H_{11}$, c-$C_7H_{13}$, c-$C_8H_{15}$, c-$C_9H_{17}$, c-$C_{10}H_{19}$, $SO_2C_6H_5$ and $SO_2$c-$C_7H_{13}$.

17. The compound of claim 16 wherein $R_1$ is H and $R_2$ is c-$C_9H_{17}$, including tautomeric forms thereof and physiologically acceptable salts thereof.

18. The compound of claim 16 wherein $R_1$ is H and $R_2$ is c-$C_8H_{15}$, including tautomeric forms thereof and physiologically acceptable salts thereof.

19. The compound of claim 16 wherein $R_1$ is H and $R_2$ is (S)CH(CH$_3$)C$_6$H$_5$, including tautomeric forms thereof and physiologically acceptable salts thereof.

20. The compound of claim 16 wherein $R_1$ is H and $R_2$ is c-$C_{10}H_{19}$, including tautomeric forms thereof and physiologically acceptable salts thereof.

21. The compound of claim 16 wherein $R_1$ is H and $R_2$ is CH$_2$C$_6$H$_5$, including tautomeric forms thereof and physiologically acceptable salts thereof.

22. The compound of claim 16 wherein $R_1$ is H and $R_2$ is SO$_2$C$_6$H$_5$ or alkyl substituted SO$_2$C$_6$H$_5$, including tautomeric forms thereof and physiologically acceptable salts thereof.

23. The compound of claim 16 wherein $R_1$ is H and $R_2$ is (S)CH(CH$_3$)-c-C$_6$H$_{11}$, including tautomeric forms thereof and physiologically acceptable salts thereof.

24. The compound of claim 16 wherein $R_1$ is H and $R_2$ is c-$C_7H_{13}$, including tautomeric forms thereof and physiologically acceptable salts thereof.

25. The compound of claim 1 wherein the compound is selected from the group of physiologically acceptable salts consisting of hydrochloride, sodium, potassium, ammonium, calcium, phosphate, citrate and magnesium salts.

26. A process for sweetening edible products including foods, beverages, confections, chewing gums, pharmaceuticals, veterinary preparations and toilet, cosmetic and hygiene products, characterized in that it comprises adding to the substance an effective sweetening amount of a compound of claim 1.

27. Edible products sweetened according to the process of claim 26.

28. Sweetening compositions characterized in that they comprise an effective sweetening amount of a compound of claim 1 and a physiologically acceptable carrier therefor.

29. The sweetening compositions of claim 28 wherein the carrier is a bulking agent.

30. The sweetening composition of claim 28 wherein the carrier is selected from the group consisting of polydextrose, starch, malto-dextrins, cellulose, methylcellulose, carboxymethylcellulose, maltitol, hydroxymethylcellulose, microcrystalline cellulose, sodium alginate, pectins, gums, lactose, maltose, glucose, leucine, glycerol, mannitol, sorbitol, sodium bicarbonate and phosphoric, citric, tartaric, fumaric, benzoic, sorbic, propionic acids and their sodium, potassium and calcium salts and mixtures of any of the above.

31. A sweetening composition comprising:
(a) a compound of claim 1; and
(b) a different sweetening agent.

32. The sweetening composition of claim 31 further comprising a bulking agent.

33. The sweetening composition of claim 31 wherein the different sweetening agent is selected from the group consisting of sucrose, corn syrups, fructose, aspartame, alitame, neohesperidin dihydrochalcone, high fructose corn syrup, hydrogenated isomaltulose, stevioside, L-sugars, glycyrrhizin, xylitol, acesulfam-K, saccharin (sodium, potassium or calcium salt), cyclamic acid (sodium, potassium or calcium salt), trichlorogalactosucrose, monellin and thaumatin and mixtures thereof.

34. A compound of the formula

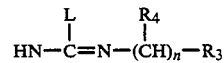

wherein
L is S-alkyl, O-alkyl, OSO$_2$-aryl, SO$_3$H or halogen, and
$R_3$, $R_4$ and n are as defined in claim 1.

35. The compound of claim 34 wherein L is S—O$_3$H or S—CH$_3$ and $R_4$ is H.

36. The compound of claim 35 wherein $R_3$ is —COOH and n is 1.

37. The compound of claim 35 wherein $R_3$ is 5-tetrazolyl and n is 1.

38. The compound of claim 36 wherein L is SO$_3$H.

39. The compound of claim 37 wherein L is SO$_3$H.

40. A process comprising:
(a) reacting a compound of the formula

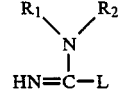

with a compound of the formula

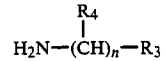

wherein
L is S-alkyl, O-alkyl, OSO$_2$-aryl, SO$_3$H or halogen and
$R_1$, $R_2$, $R_3$, $R_4$ and n are as defined in claim 1 under conditions sufficient to form the corresponding guanidine and
(b) recovering the guanidine compound formed in (a) above.

41. The process of claim 40 wherein L is —S—CH$_3$ or —SO$_3$H.

42. The process of claim 40 wherein n is H and $R_1$, $R_4$ and $R_5$ are H.

43. The process of claim 42 wherein $R_2$ is cyclohexyl, cyclooctyl, alpha-phenethyl, benzyl, SO$_2$C$_6$H$_5$, alkyl substituted SO$_2$C$_6$H$_5$ or phenyl.

* * * * *